United States Patent [19]
Yerkovich et al.

[11] Patent Number: 5,716,380
[45] Date of Patent: Feb. 10, 1998

[54] COMMON THERAPY/DATA PORT FOR A PORTABLE DEFIBRILLATOR

[75] Inventors: Daniel Yerkovich, Snohomish; David Aoyama, Seattle; Stephen T. Vincent, Redmond, all of Wash.

[73] Assignee: Physio-Control Corporation, Redmond, Wash.

[21] Appl. No.: 632,177

[22] Filed: Apr. 15, 1996

[51] Int. Cl.⁶ .................................................... A61N 1/39
[52] U.S. Cl. .................................................... 607/5; 607/2
[58] Field of Search .................................. 607/5, 2, 4, 9, 607/10, 27, 142, 32, 60; 128/709, 710, 705, 903

[56] References Cited

U.S. PATENT DOCUMENTS

| | | |
|---|---|---|
| 4,094,310 | 6/1978 | McEachern et al. . |
| 4,096,856 | 6/1978 | Smith et al. . |
| 4,102,332 | 7/1978 | Gessman . |
| 4,106,494 | 8/1978 | McEachern . |
| 4,210,149 | 7/1980 | Heilman et al. . |
| 4,223,678 | 9/1980 | Langer et al. . |
| 4,475,551 | 10/1984 | Langer et al. . |
| 4,619,265 | 10/1986 | Morgan et al. . |
| 4,628,935 | 12/1986 | Jones et al. . |
| 4,653,747 | 3/1987 | Reithler . |
| 4,830,006 | 5/1989 | Haluska et al. . |
| 4,928,674 | 5/1990 | Halperin et al. . |
| 5,014,701 | 5/1991 | Pless et al. . |
| 5,105,821 | 4/1992 | Reyes . |
| 5,222,480 | 6/1993 | Couche et al. . |
| 5,249,573 | 10/1993 | Fincke et al. . |
| 5,275,158 | 1/1994 | Lopin . |
| 5,342,403 | 8/1994 | Powers et al. . |
| 5,374,279 | 12/1994 | Duffin, Jr. et al. . |
| 5,391,187 | 2/1995 | Freeman . |
| 5,441,518 | 8/1995 | Adams et al. . |
| 5,441,520 | 8/1995 | Olsen et al. . |

Primary Examiner—William E. Kamm
Assistant Examiner—Kennedy J. Schaetzle
Attorney, Agent, or Firm—Christensen O'Connor Johnson & Kindness PLLC

[57] ABSTRACT

A portable defibrillator (10) with a common therapy/data port (12). A set of electrodes (34) is connected to the therapy/data port to connect the defibrillator to a patient. If connected to a patient, the defibrillator operates in a normal mode of operation where it analyzes a patient's electrocardiogram (ECG), and, if required, applies defibrillation therapy through the port to the patient. A communication cable (42) is connected to the therapy/data port to connect the defibrillator to an auxiliary component (44). If connected to an auxiliary component, the defibrillator operates in a data communication mode of operation where data may be transmitted to and received from the auxiliary component through the therapy/data port. A test cable is connected to the therapy/data port to connect the defibrillator to a test load. If connected to a test load, the defibrillator operates in a user test mode of operation to allow a user to test the operation of the defibrillator. Preferably, the portable defibrillator automatically determines whether it is connected to a patient, an auxiliary component, or a test load.

20 Claims, 6 Drawing Sheets

COMMON THERAPY/DATA PORT FOR A PORTABLE DEFIBRILLATOR

FIELD OF THE INVENTION

This invention generally relates to portable electronic physiological instruments, and more specifically to data and therapy ports for a portable defibrillator.

BACKGROUND OF THE INVENTION

It is well known that the probability of surviving a heart attack depends on the speed with which appropriate medical care is provided. One of the most common and life-threatening consequences of a heart attack is the development of a cardiac arrhythmia such as a ventricular fibrillation in which the heart is unable to pump a sufficient volume of blood. When such an arrhythmia occurs, serious brain damage and death will invariably result unless a normal heart rhythm can be restored within a few minutes.

The most effective treatment for ventricular fibrillation is the application of a strong electric shock to the victim. The electric shock frequently terminates the chaotic activity characteristic of arrhythmias, and restores the normal pumping action of the heart. Defibrillators for producing and delivering such shocks have been known and successfully used for many years. However, the size and cost of prior defibrillators, coupled with the risk they pose if used improperly, have restricted the use of defibrillators to emergency medical technicians (EMTs) and other trained emergency personnel.

Recently, it has been recognized that a greater number of heart attack victims could be saved if those persons who are typically first to arrive at a medical emergency, including fire fighters, the police, and even the public (hereinafter collectively referred to as "first responders"), were provided with portable defibrillators. Because of the reduced level of expertise of the first responder group, a portable defibrillator provided to the first responders should be as simple as possible. Reducing the complexity of the portable defibrillator ensures that even in stressful emergency situations, the first responder could successfully connect the defibrillator to the patient and apply a defibrillation pulse. A first responder defibrillator should therefore be designed to be as user friendly as possible.

An important feature that exists in many portable as well as non-portable defibrillators is the ability to record data surrounding a defibrillation event for later analysis. The data may include electrocardiogram (ECG) data from the patient, event data corresponding to functions implemented by a defibrillator user, and voice or other data recorded at the site of the emergency. The preferred method of accessing the stored data is to later download it through a dedicated data port located on the defibrillator. To download the data, a communication cable is connected between the dedicated data port on the defibrillator and a communication port on a computer. Data surrounding the defibrillation event is then downloaded to the computer where it may be stored for later analysis.

Unfortunately, the inclusion of a dedicated data port on a portable defibrillator poses a variety of problems, especially in a defibrillator used by a first responder. Most defibrillators have a therapy port through which defibrillation signals are applied to a patient. A set of electrodes is plugged into the therapy port, and a defibrillation pulse is applied to the patient through the electrodes. Although skilled users of portable defibrillators receive extensive training as to the proper identity of the ports on the defibrillator, first responders may not have received such extensive training, or may have a tendency to forget such training during the confusion surrounding an emergency. When confronted with two ports on the defibrillator, an unskilled user may therefore easily confuse the ports and attempt to plug the set of electrodes into the data port. Alternatively, the user may attempt to plug the communication cable into the therapy port. A first responder defibrillator should therefore not have two ports since a user could easily confuse the port used to apply a defibrillation pulse to a patient with the port used to transmit data to a computer.

Moreover, defibrillators generate extremely high voltages when applying a defibrillation pulse to a patient. A dedicated data port inherently increases the mount of exposed metal on the exterior of the unit, thereby increasing the chance that a short within the defibrillator could reach an operator in contact with the data port. Defibrillators with separate therapy and data ports therefore require special shielding or additional circuitry to minimize the potential of inadvertent shocks.

Finally, portable defibrillators are used in a variety of outdoor conditions in which they are subject to water, dirt, dust, and other contaminants. Portable defibrillators should therefore be water-tight to protect internal circuits from damage or internal shorts. A defibrillator with multiple ports is more costly to construct due to the seals required to maintain the water-tight integrity of more than one port.

The present invention is directed to overcoming the foregoing and other disadvantages. More specifically, the present invention is directed to reducing the number of ports in a portable defibrillator, thereby increasing the level of water-tight integrity, decreasing the likelihood of the operator being shocked by the device, and reducing the likelihood of first responder confusion during emergency situations.

SUMMARY OF THE INVENTION

In accordance with this invention, a portable defibrillator with a common therapy/data port is provided. The portable defibrillator analyzes a patient's electrocardiogram (ECG) and applies a selected therapy based on the ECG and user input. The defibrillator includes means to detect a patient's ECG, store episode data corresponding to the ECG, and analyze the ECG to determine a type of therapy to apply to the patient. A therapy generator is provided in the defibrillator to generate a defibrillation signal that may be applied to the patient in accordance with the analyzed ECG. A communication interface is also provided in the defibrillator to transmit the stored episode data to an externally connected auxiliary component. The common therapy/data port is connected to the communication interface and to the therapy generator. The port allows application of therapy signals to the patient, transmission of stored episode data to the auxiliary component connected to the port, and testing of the defibrillator.

In accordance with one aspect of the invention, the defibrillator detects whether a patient, a test load, or an auxiliary component is connected to the defibrillator. The presence of a patient or a test load is initially determined by measuring the impedance of the connected device. If a patient or test load is not detected, the type of auxiliary component is determined from the transmission and receipt of identification signals, or by user input. Various types of auxiliary components may be connected to the defibrillator, including a test instrument, a modem, a computer, a printer, or other data storage or data display device. Preferably, the defibrillator automatically determines whether a patient, test load, or auxiliary component is connected to the therapy/data port.

In accordance with another aspect of the invention, the defibrillator may enter one of several modes of operation depending on whether a patient, a test load, or an auxiliary component is connected to the defibrillator. When a patient is detected, the defibrillator enters a normal mode of operation where the patient's ECG is analyzed and appropriate therapy applied to the patient. When a test load is detected, the defibrillator enters a user test mode of operation to allow the operation of the defibrillator to be tested. If an auxiliary component is detected, the defibrillator enters a data communication mode of operation wherein data is transferred between the defibrillator and the auxiliary component.

In accordance with yet another aspect of the invention, protection circuitry coupled between the communication interface and the common therapy/data port protects the communication interface from induced voltages and currents when therapy is being applied to the patient. Limiting the voltage and current applied to the communication interface when therapy is provided to the patient prevents the communication interface from being damaged during operation. The protection circuitry also prevents the interface from being damaged from electrostatic discharge.

It will be appreciated that several advantages arise from the inclusion of a common therapy/data port in a portable defibrillator. Perhaps most importantly, the common therapy/data port simplifies the use of the defibrillator. Regardless of whether a patient, a test load, or an auxiliary component is connected to the defibrillator, the connection is made at the single port. By simplifying the defibrillator operation, the device becomes usable by first responders having little or no formal training. The common therapy/data port also reduces the overall cost of the defibrillator. The therapy/data port only requires a single seal to ensure water-tight integrity, and eliminates the shielding or circuitry required to protect the operator from potential shocks.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
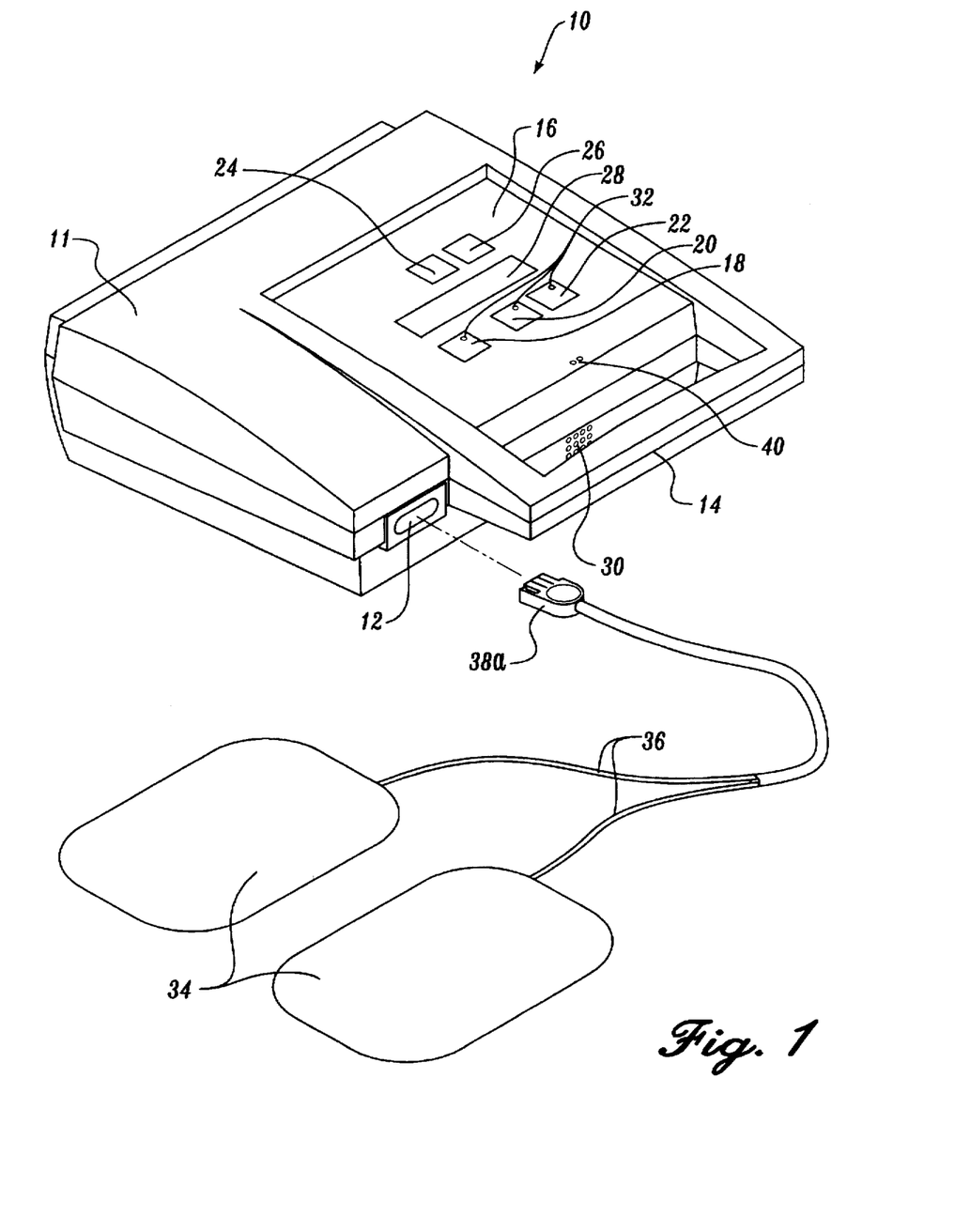
FIG. 1 is a perspective view of a portable defibrillator having a common therapy/data port formed in accordance with the present invention.

FIG. 1 depicts a portable defibrillator 10 formed in accordance with the present invention and designed for use by a first responder during a medical emergency. To facilitate use in the field, defibrillator 10 is formed with an impact resistant plastic case 11 having an integral handle 14 to allow the user to easily carry the defibrillator to a desired location. When used, the defibrillator is preferably positioned so that a control panel 16 on the defibrillator is oriented upwards towards the user. Control panel 16 contains a simplified interface to minimize the amount of keyed entry required to operate the defibrillator. Five buttons are present on the control panel: an on/off button 18, an analyze button 20, a shock button 22, and two arrow buttons 24 and 26. The function of each button will be described in additional detail below. The defibrillator provides instructions or other information to the user using several different displays. A liquid crystal display (LCD) 28 display instructions to the user to direct the user to perform different tasks, e.g. "press analyze." A speaker 30 is integrally formed in the case of the defibrillator to allow the defibrillator to provide a corresponding verbal command to the user. Several LEDs 32 are also provided to indicate the status of the defibrillator, such as whether an energy storage capacitor within the defibrillator is sufficiently charged to provide a defibrillation pulse to a patient.

Located adjacent the handle 14 of the defibrillator is a therapy/data port 12. The therapy/data port is used to connect the defibrillator to a patient, to an auxiliary component, or to a test load. Although many different connectors could be designed to mate with the therapy/data port 12, preferably a QUIK-COMBO™ connector sold by Physio-Control Corporation of Redmond, Wash. is used to mate with the port. A QUIK-COMBO connector 38 is depicted in isolation with therapy/data port 12 in FIG. 3. Connector 38 is constructed with a body 46 having three non-conductive fingers 48a, 48b, and 48c that extend parallel with the path that the connector must mate with therapy/data port 12. The connector may contain up to four conductive pins. Each of the outer fingers 48a and 48c may contain a single conductive pin, while the inner finger 48b is formed to accept two conductive pins. Each finger is formed of a non-conductive plastic to act as a shield and prevent shorting between conductive pins. The fingers mate with a corresponding socket in therapy/data port 12. The body 46 of the connector is also formed with a locking latch 50 that extends generally parallel with the mating path. The locking latch contains a lip 52 that latches over a complementary tab in the therapy/data port to prevent the connector from being inadvertently pulled from the port. The locking latch also serves as a key to prevent the connector 38 from being incorrectly inserted into the therapy/data port.

Figure 3:
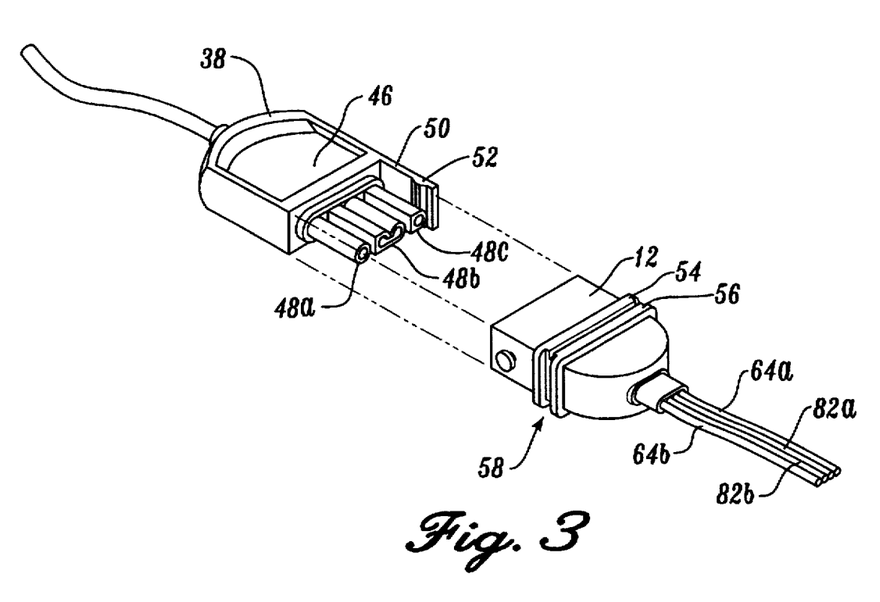
FIG. 3 is a perspective view of a connector that connects to the common therapy/data port.

The body of therapy/data port 12 is formed of a non-conductive resilient material to mate with connector 38. The therapy/data port contains two therapy lines 64a and 64b and two data lines 82a and 82b that are connected to conductive receptacles in the therapy/data port. When mated with the connector 38, each of the conductive receptacles receives a corresponding conductive pin in the inner or outer fingers, assuming such a conductive pin is present. The therapy/data port 12 is also formed with two integral seals 54 and 56 that extend around the body of the port. Seals 54 and 56 form a slot 58 surrounding the port into which a portion of the defibrillator plastic case 11 may extend. The seals prevent water, dirt, or other contaminants from entering the defibrillator.

The number of conductive pins in connector 38 varies depending upon whether the connector is used to connect a set of electrodes, a communication cable, or a test cable to the defibrillator. Returning to FIG. 1, when the connector (designated connector 38a) is used with a set of electrodes, the two outer fingers 48a and 48c each contain a conductive pin. Each of the conductive pins is connected to one of a set of electrodes 34 by a lead 36. The inner finger 48b does not contain any conductive pins. Although various types of electrodes may be used with defibrillator 10, preferably the electrodes are QUIK-COMBO™ pacing/defibrillation/ECG electrodes sold by Physio-Control Corporation. QUIK-COMBO electrodes are disposable electrodes that are applied to the patient by peeling away a backing on the electrodes to expose an adhesive pad. To connect the electrodes to the defibrillator, connector 38a is inserted into the therapy/data port.

When connected to a patient, the defibrillator operates in a normal mode of operation. A first responder places the electrodes on the patient, inserts the QUIK-COMBO connector into the therapy/data port, and turns the defibrillator on by depressing the on/off button 18. Upon detecting the patient, using a technique described below, the defibrillator enters the normal mode of operation. Following the instructions provided by the defibrillator, the first responder initially presses the analyze button 20. After the analyze button has been pressed, the defibrillator analyzes the electrocardiogram (ECG) of the patient to determine if defibrillation therapy should be applied to the patient. If an arrhythmia is detected, the defibrillator notifies the first responder with both a visual and auditory warning. The defibrillator then automatically charges the energy storage capacitor to a predetermined voltage. When an appropriate charge is reached, the first responder is instructed to press the shock button 22 in order to apply a defibrillation pulse to the patient through the set of electrodes 34. While other features of the defibrillator are available to the user, a full discussion of the defibrillator operation is not necessary for an understanding of the present invention.

During therapy, defibrillator 10 stores episode data surrounding the emergency. The episode data typically includes the continuous ECG of the patient, and a summary of the ECG immediately before and after a defibrillation pulse is applied to a patient. The latter data is preferably formatted according to the CODE SUMMARY™ standard adopted by Physio-Control Corporation in their line of portable defibrillators, monitors, and pacers. The episode data may also include other data, including a time index of when defibrillation pulses were applied to the patient, the energy of each pulse, patient impedance data, and other patient and system events necessary to reconstruct the defibrillation therapy. Moreover, the episode data may even contain the scene audio, recorded using a microphone 40 that is incorporated in the body of the defibrillator. Those skilled in the art will recognize that the type of episode data that may be recorded is only limited by the external sensors provided in the defibrillator, and the amount of storage available within defibrillator 10. Compression techniques may be used to compress the ECG and other data in order to maximize the amount of episode data that may be stored.

Figure 2:
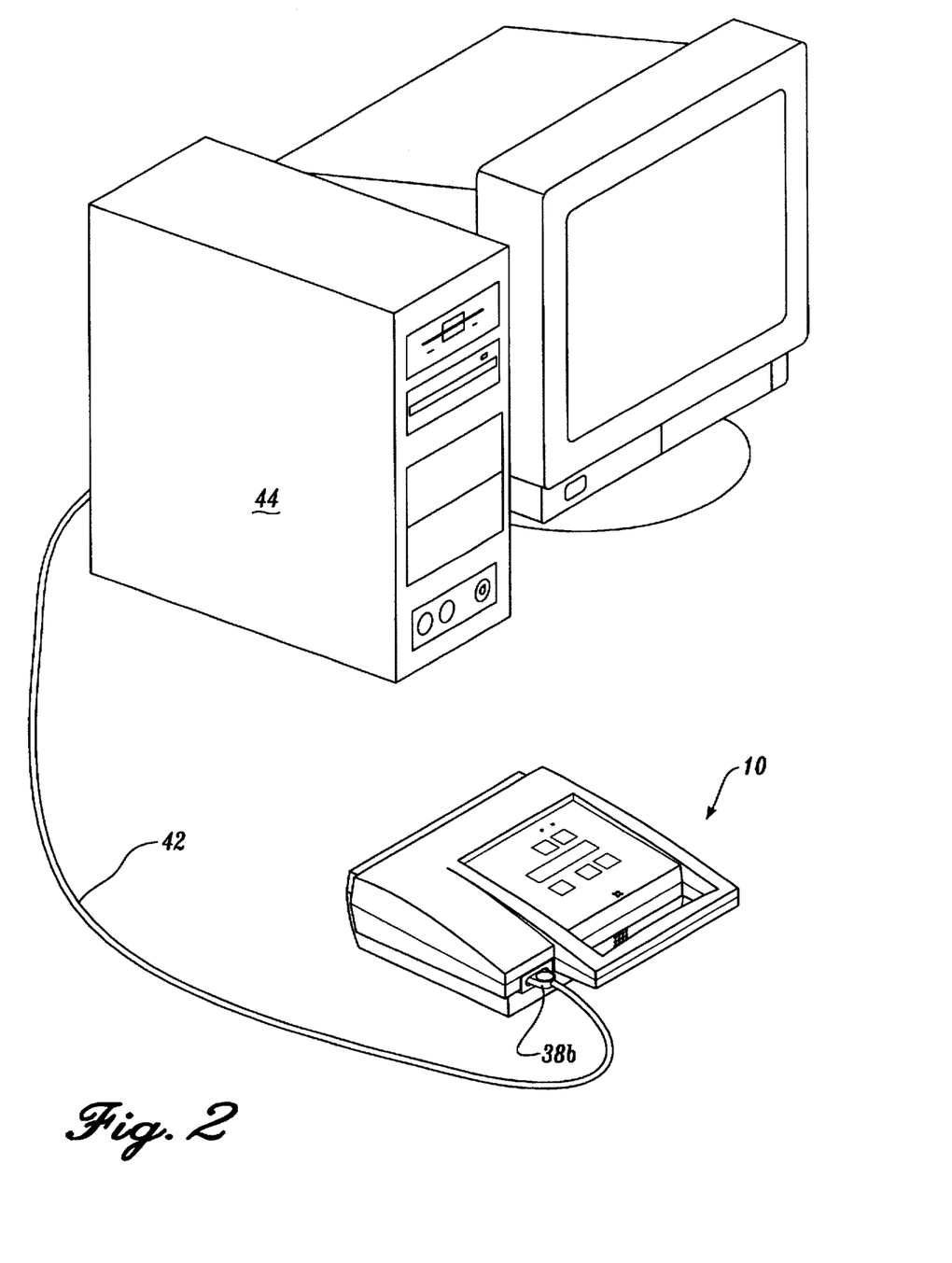
FIG. 2 is a perspective view of the portable defibrillator of the present invention coupled to an auxiliary component.

The episode data may later be downloaded from defibrillator 10 to an auxiliary component in order to analyze the results of the particular therapy applied to the patient, and to develop a database from which the efficacy of treatment over a large number of patients may be studied. To connect the defibrillator 10 to an auxiliary component 44, a communication cable 42 is connected between the defibrillator and the auxiliary component as shown in FIG. 2. Although the auxiliary component is depicted as a personal computer in FIG. 2, it will be appreciated that the auxiliary component may also be any of a number of devices that would allow the data to be stored or reviewed. For example, the auxiliary component may be a printer to print a hard copy of the episode data, a modem to transmit the episode data to a remote computer, or a hard disk drive or other storage medium to store the episode data.

To connect the communication cable 42 to the defibrillator therapy/data port, the cable is provided with a QUIK-COMBO connector (designated connector 38b) that contains three conductive pins. The inner finger 48b contains two conductive pins and the outer finger 48a contains a single conductive pin. Finger 48c does not contain a conductive pin in the communication cable connector. The three conductive pins in the connector 38b are coupled to wires within cable 42. The other end of cable 42 is wired with a connector (not shown) that is selected as required to mate with the auxiliary component.

When connected to an auxiliary component, the defibrillator identifies the auxiliary component and operates in a data communication mode of operation. In the data communication mode, data may be downloaded to the auxiliary component for printing storage, or review. Data may also be uploaded to the defibrillator to govern the data transfer, perform tests of the defibrillator, or modify the software within the defibrillator.

Most modern defibrillators are also equipped with a test mode so that the operation of the defibrillator may be easily tested by a user. To test the defibrillator, a test load of typically 50 ohms is connected to the defibrillator. The energy storage capacitor is then charged and discharged into the test load in order to verify the correct operation of the device. The test load may also be used to train the first responder in the use of the device without having to connect the defibrillator to a patient. To connect the defibrillator to a test load, a test cable is provided having a QUIK-COMBO connector 38 with four conductive pins. Conductive pins in each of the outer fingers 48a and 48c are connected to the 50 ohm test load. Two conductive pins in the inner finger 48b are shorted together. As discussed in additional detail below, upon detecting a test load connected to the defibrillator, the defibrillator automatically enters a user test mode of operation.

It will be appreciated that the use of a common therapy/data port greatly simplifies the operation of the defibrillator. When responding to an emergency, the first responder immediately recognizes where to connect the set of electrodes to the defibrillator. No confusion arises due to the presence of multiple ports on the defibrillator. Further, since the connectors used to connect the set of electrodes, communication cable, or test cable are shaped substantially the same, the first responder may be easily trained in the use of the defibrillator.

Figure 4:
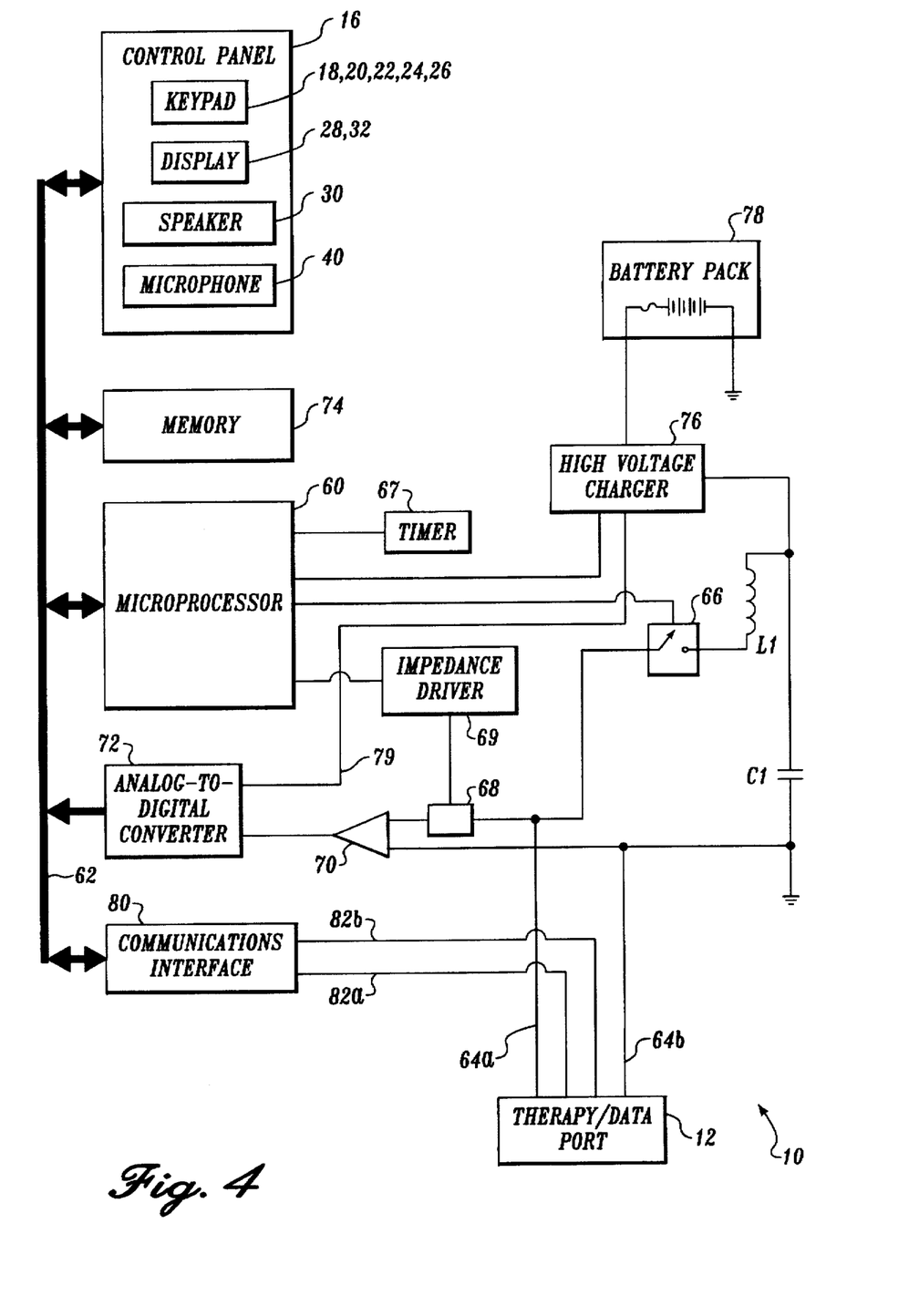
FIG. 4 is a block diagram of the portable defibrillator hardware, including a communication interface coupled to the common therapy/data port.

In order for a common therapy/data port to be incorporated in defibrillator 10, appropriate changes must be made to both the hardware and the software of the defibrillator. FIG. 4 is a block diagram of the hardware within defibrillator 10. At the heart of the defibrillator is a microprocessor 60. While only a single microprocessor is shown, it will be appreciated that preferably dual microprocessors are incorporated in the defibrillator to provide redundancy and enhance processing capability. Microprocessor 60 is connected to the control panel 16 by a bus 62. The microprocessor can therefore receive commands generated by a first responder using buttons 18, 20, 22, 24, and 26 on the control panel. Voice data received on the microphone 40 can also be digitized and stored using techniques known in the art. To provide instructions or visual cues to the user, the microprocessor can transfer via bus 62 appropriate data to activate the LCD display 28, LEDs 32, or provide voiced commands over speaker 30.

In the normal mode of operation, the microprocessor is responsible for analyzing the ECG of the patient to determine if a shockable rhythm is detected, and if so, to charge an energy storage capacitor for application of a defibrillation shock to the patient. The ECG is detected from the patient via the set of electrodes, and provided to the defibrillator through the common therapy/data port. Two therapy lines 64a and 64b are connected to the therapy/data port 12 to distribute the ECG signal within the defibrillator. Line 64b is a return line, while line 64a is connected to a discharge switch 66 and a transient protection circuit 68.

To manipulate the analog ECG signal within the defibrillator, the signal must be converted into digital form. The transient protection circuit 68, a preamplifier 70, and an analog-to-digital converter 72 are coupled between line 64a and the microprocessor to digitize the ECG. The transient protection circuit ensures that the preamplifier will not be damaged when defibrillation pulses are applied to the patient over therapy lines 64a and 64b. Preamplifier 70 amplifies the ECG signal and provides it to the analog-to-digital converter 72 where it is digitized. As the ECG signal is received, it is analyzed by the microprocessor and stored as a portion of the episode data for later retrieval. Although various storage media such as computer tapes could be used to store the episode data, in an actual embodiment of the invention the ECG and other episode data is stored within a memory 74. Preferably, a portion of memory 74 is non-volatile memory so that the data will be retained even though the power to the defibrillator is later turned off during transport.

If a shockable rhythm is detected during analysis of the ECG, the microprocessor charges an energy storage capacitor C1 in anticipation of applying a defibrillation pulse to the patient. To charge the capacitor, appropriate commands are provided to a high voltage charger circuit 76, located between the energy storage capacitor and a battery pack 78. The voltage across the capacitor is measured on a line 79 which is connected to the analog-to-digital converter 72. When the voltage reaches the desired level, the LED on the shock button 22 is lit to indicate to the first responder that the defibrillator is ready to apply a defibrillation shock to the patient. If the first responder depresses shock button, indicating that the shock should be applied, the microprocessor closes discharge switch 66. Closing discharge switch 66 connects the energy storage capacitor C1 to the patient over therapy lines 64a and 64b, applying a defibrillation pulse to hopefully halt the patient's arrhythmia. An inductor L1 is provided in the discharge path to shape the defibrillation pulse as the pulse is applied to the patient. If the defibrillation pulse fails to halt the patient's arrhythmia, the process of charging and discharging the energy storage capacitor is repeated.

At the completion of administering therapy to the patient, memory 74 contains episode data that corresponds to the applied therapy. As discussed above, the episode data may contain ECG data, CODE SUMMARY data, voice data, and other information. To allow analysis of the episode data by subsequent caregivers, the data must be downloaded from the defibrillator 10. To download the data, the defibrillator is connected to an auxiliary component as depicted in FIG. 2. When the connection is completed, the microprocessor may transmit the data to the auxiliary component via a communication interface 80. As shown in FIG. 4, the communication interface is connected to the therapy/data port 12 by a pair of data lines 82a and 82b.

Figure 5:
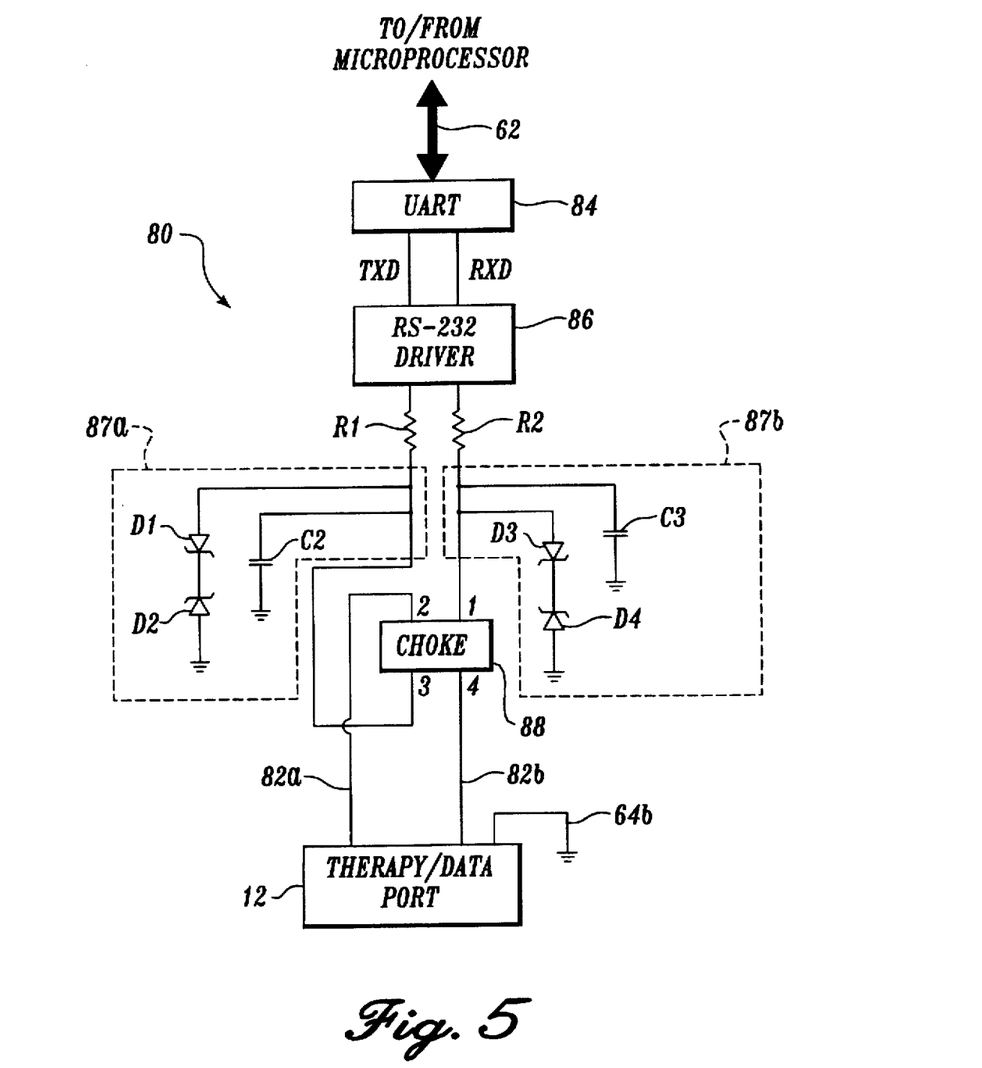
FIG. 5 is a schematic of the communication interface, including a protection circuit for protecting the communication interface during application of therapy to a patient.

FIG. 5 is a schematic of the communication interface 80 used to couple microprocessor 60 to the therapy/data port 12. Parallel data is provided from the microprocessor over bus 62 to a universal asynchronous receiver/transmitter (UART) 84. The UART handles parallel to serial conversion of the data for transmission purposes, and provides the serial data to an RS-232 driver 86 over a transmit line TXD. The RS-232 driver steps up the voltage level of the data signal for transmission over cable 42 to the auxiliary component. The RS-232 driver also steps down the voltage level of received signals and provides the received data to the UART over a receive line RXD.

The RS-232 driver 86 is connected to the therapy/data port 12 through clamping circuits 87a and 87b and a choke 88. Clamping circuit 87a comprises a resistor R1 in series with the data line 82a, a Zener diode pair D1 and D2 coupled cathode to cathode between the data line 82a and ground, and a capacitor C2 coupled between the data line 82a and ground. The purpose of the clamping circuit is to limit the voltage that is applied to the RS-232 driver. Although the defibrillation pulse is carried on therapy lines 64a and 64b, rather than data lines 82a and 82b, the proximity of the therapy lines to the data lines where the lines pass through the therapy/data port may cause a voltage pulse to be induced on the data lines. Clamping circuit 87a prevents the induced voltage pulse on the transmit data line from damaging the RS-232 driver. The clamping circuit also protect the RS-232 driver from electrostatic discharge (ESD). Clamping circuit 87b, has a similar construction to clamping circuit 87a, with a resistor R2, capacitor C3, and diodes D3 and D4 coupled to data line 82b. Clamping circuit 87b prevents ESD and the induced voltage pulse on the receive data line from damaging the RS-232 driver. Both the transmit and the receive data lines also pass through a ferrite bead choke 88. The choke limits the amount of electromagnetic interference (EMI) generated as the signals are transmitted over cable 42 connected to the therapy/data port.

When in data communication mode, therapy line 64b is used as a return to ground. The three wire interface (TXD, RXD and return) between the defibrillator and the auxiliary component is sufficient to allow serial data transfer rates up to or exceeding 115 kbaud. Those skilled in the art will recognize that due to the lack of dedicated handshaking lines in the interface, handshaking between the defibrillator and the auxiliary component must be performed in software.

Returning to FIG. 4, the defibrillator is also provided with circuitry to measure the impedance across the therapy lines 64a and 64b. Several different techniques are recognized for measuring the impedance of a patient and the electrodes attached to the patient. In an actual embodiment of the invention, an impedance driver 69 is provided to generate a high frequency AC signal. The high frequency AC signal is applied through the transient protection circuit 68 to therapy line 64a. Using a technique that is known in the art, the impedance across the therapy lines is determined from the amplitude of a corresponding received AC signal that is filtered from the patient's EGG. A timer 67 is also provided in the defibrillator in order to provide an accurate timebase to the microprocessor 60.

In order to determine whether to operate in the normal mode, the data communication mode, or the user test mode, the defibrillator must be able to identify whether a patient, an auxiliary component, or a test load is connected to the therapy/data port. A preferred software routine 100 for detecting the identity of the item connected to the therapy/data port is provided in FIG. 6.

Figure 6:
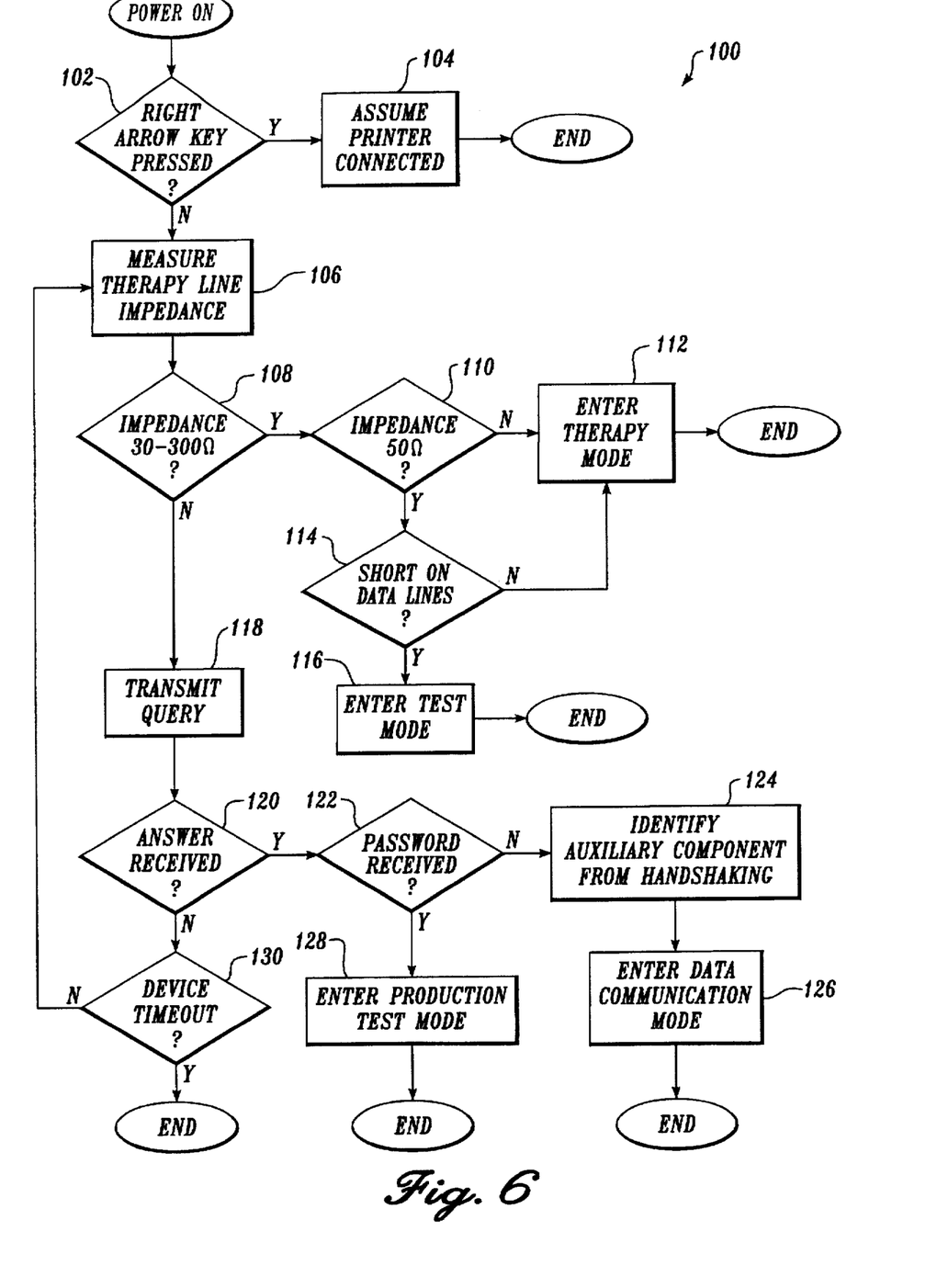
FIG. 6 is a flow chart of a preferred routine for determining whether a patient, an auxiliary component, or a test load is coupled to the portable defibrillator.

As depicted in FIG. 6, immediately after the defibrillator is powered on a test is made at a decision block 102 to determine if the right arrow button 26 was pressed as the defibrillator was turned on. If the right arrow button was pressed as the defibrillator was turned on, at a block 104 the routine assumes that a printer is connected to the therapy/data port and begins to transmit stored episode data in a format for printing. It will be appreciated that determining whether a printer is connected to the defibrillator must be based on input from the user because some commonly available printers do not provide an output that could be used to identify the printer. Determining whether other devices or a patient are connected to the defibrillator is, however, performed automatically as discussed below.

If the right arrow button was not depressed by a first responder during power up, at a block 106 a measurement is made of the impedance across the therapy lines 64a and 64b. The impedance is measured by application of the high frequency AC signal from impedance driver 69. At a decision block 108, a test is made of the measured impedance. If the measured impedance falls within a range of 30–300 ohms, the routine continues to a decision block 110. If the measured impedance falls outside of the 30–300 ohm range, the routine continues to a block 118. The range of 30–300 ohms is preselected to encompass the expected range of patient impedances.

At decision block 110, a test is made to determine if the therapy line impedance is 50 ohms. If the therapy line impedance is not 50 ohms, the routine continues to a block 112. At block 112, the defibrillator enters the normal mode of operation. That is, the detected impedance on the therapy lines indicates that a patient may be connected to the defibrillator. The defibrillator therefore attempts to detect an ECG of the patient on the therapy lines. If the ECG is detected, an analysis is performed and appropriate treatment initiated.

If the therapy line impedance is 50 ohms at decision block 110, a test is made to determine if the user of the defibrillator is attempting to enter the user test mode. To indicate that the defibrillator is to enter the user test mode, the test cable connector is constructed with the data leads 82a and 82b shorted together. At decision block 114, a test is therefore made to determine if the data lines are shorted together by transmitting a signal on the TXD line and attempting to receive the signal on the RXD line. If the data lines are shorted, at a block 116 the defibrillator enters the user test mode. If the data lines are not shorted, at a block 112 the defibrillator enters the normal mode since the detected impedance falls within a range indicating that a patient may be connected to the defibrillator. It will be appreciated that other techniques could also be used to indicate that the defibrillator is to enter a user test mode, including depressing an appropriate sequence of buttons on the defibrillator control panel.

Returning to decision block 108, if the detected therapy line impedance falls outside the range of 30–300 ohms, the routine proceeds to block 118. At block 118, a query is transmitted by the defibrillator over data lines 82a and 82b. The query may take a variety of forms, but is designed to elicit a handshaking response from an auxiliary component connected to the defibrillator through the therapy/data port. At a decision block 120, a test is made to determine if an answer to the query is received. If an answer is received, at a decision block 122 a test is made to determine if the answer contains a special password. If a password is contained in the answer, at a block 128 the defibrillator enters a production test mode of operation. The production test mode is used by the manufacturer after assembly of the defibrillator or during later servicing. In the production test mode, data may be transmitted between test equipment and the defibrillator in order to run the defibrillator through a suite of tests. During the tests, it is possible to have the defibrillator alternate between the normal mode of operation and the data communication mode of operation in order to fully test the defibrillator.

If a password in not contained in the answer at decision block 122, the routine continues to a block 124. At block 124 the type of auxiliary component connected to the defibrillator is determined based on identification signals contained in the answer. As discussed above, the auxiliary component may be a computer or a modem to allow transmission of the episode data to a remote computer. After identifying the attached auxiliary component, the defibrillator enters the data communication mode at block 126. In the data communication mode, episode data, test data, or other data is transmitted to and received from the auxiliary component.

Returning to decision block 120, if an answer is not received within an appropriate span of time, the routine continues to a decision block 130. At decision block 130 the amount of time that the defibrillator has been waiting to detect either a patient, an auxiliary component, or a test load is examined. If a connection to the defibrillator has not been detected within a preselected timeout period, the defibrillator halts attempting to detect a connection and automatically powers down. Automatically powering down conserves battery power in the event that the defibrillator was inadvertently turned on. If the timeout period has not expired, the routine returns to block 106 where another measurement of the therapy line impedance is performed. In this manner, the routine will automatically cycle through attempting to detect a connection to a patient, an auxiliary component, or a test load for the duration of the timeout period.

It will be appreciated that the use of a single port for both data communication and application of therapy to a patient offers several manufacturing advantages over a defibrillator with dedicated ports for each function. A single port reduces the cost of the defibrillator by making it easier to waterproof the defibrillator body. The single port also minimizes the number of connections between the internal circuitry and the external case of the defibrillator, making it easier to prevent shocks from occurring from external connectors.

While the preferred embodiment of the invention has been illustrated and described, it will be appreciated that various changes can be made therein without departing from the spirit and the scope of the invention. For example, while it is contemplated that a commonly shaped connector 38 is used to connect the set of electrodes, the communication cable, and the test cable to the therapy/data port, it will be appreciated that differently shaped connectors may be used to connect each item with the defibrillator. A commonly shaped connector, however, simplifies use by a first responder.

It will also be appreciated that while only two data lines and the return are used during the data communication mode, the number of data lines could be expanded to increase the data communication rate and to provide dedicated handshaking lines. An expansion of the number of data lines would require a redesign of communication interface 80 to provide the appropriate interface between the microprocessor and the auxiliary component. Connector 38 would also have to be expanded to include an additional number of conducting pins. The number of data lines may also be reduced to a single data line and a return line. Reducing the number of data lines would, however, decrease the data communication rate.

Those skilled in the art will further recognize that while the common therapy/data port was disclosed in the context of a portable defibrillator 10, the common therapy/data port could also be incorporated in other portable or non-portable medical instruments. For example, the common therapy/data port could be incorporated in a portable pacing unit that is designed to analyze a patient's ECG and to apply pacing therapy. The design of the common therapy/data port has broad applicability to any portable or non-portable medical device that would benefit from a reduction in external ports on the device. Consequently, within the scope of the appended claims, it will be appreciated that the invention can be practiced otherwise than as specifically described herein.

The embodiments of the invention in which an exclusive property or privilege is claimed are defined as follows:

1. An external electronic physiological instrument for analyzing a patient's electrocardiogram and applying a selected therapy based on the analyzed electrocardiogram, the instrument comprising:

(a) analysis means for detecting an electrocardiogram of a patient, performing an analysis of the electrocardiogram to determine a type of therapy to apply to the patient, and storing data corresponding to the electrocardiogram;

(b) a therapy generator coupled to the analysis means for generation of a therapy signal that may be applied to the patient, the therapy signal being based on the analysis of the electrocardiogram and the determined type of therapy;

(c) communication means coupled to the analysis means for transmitting the stored data to an auxiliary component; and (d) a port connected to the communication means and to the therapy generator and allowing application of the therapy signal to the patient or transmission of the stored data to the auxiliary component.

2. The instrument of claim 1, further comprising means to determine whether the patient is connected to the port, the instrument entering a normal mode of operation if the patient is connected to the port.

3. The instrument of claim 2, wherein the therapy generator is coupled to the port through a pair of therapy lines.

4. The instrument of claim 3, wherein the means to determine whether the patient is connected to the port comprises an impedance detector for measuring an impedance across the pair of therapy lines, the detected impedance falling within a range of impedances when a patient is connected to the port.

5. The instrument of claim 3, wherein the therapy signal applied over the pair of therapy lines is a defibrillation shock.

6. The instrument of claim 1, further comprising means to detect when the auxiliary component is coupled to the port and to instruct the instrument to enter a data communication mode of operation if the auxiliary component is coupled to the port, the instrument entering the data communication mode if the auxiliary component is coupled to the port.

7. The instrument of claim 1, wherein the communication means is coupled to the port by at least one data line and a return line.

8. The instrument of claim 7, wherein the communication means transmits the stored data over the at least one data line and the return line.

9. The instrument of claim 1, wherein the communication means receives data from the auxiliary component through the port.

10. The instrument of claim 9, wherein the operation of the analysis means is varied in response to the data received from the auxiliary component.

11. The instrument of claim 1, further comprising means to detect when a test instrument is coupled to the port and to instruct the instrument to enter a test mode of operation if the test instrument is connected to the port, the instrument entering the test mode if the test instrument is connected to the port.

12. The instrument of claim 1, further comprising a protection circuit coupled between the communication means and the port to protect the communication means when therapy is applied to the patient.

13. The instrument of claim 1, wherein the auxiliary component for receiving the stored data is selected from the group consisting of a printer, a modem, a computer, or a data storage device.

14. In an electronic physiological instrument having a communication circuit, a therapy circuit, and a port, a method of selecting between a normal mode of operation wherein therapy signals are applied over a plurality of therapy leads coupled between the therapy circuit and the port, and a data communication mode of operation wherein data are transmitted over at least one data lead coupled between the communication circuit and the port, the method comprising:

(a) applying a first signal to one of the plurality of therapy leads;

(b) detecting a first responsive signal on one of the plurality of therapy leads and entering the normal mode of operation if the first responsive signal indicates that a patient is connected to the electronic physiological instrument;

(c) applying a second signal to the at least one data lead if a patient is not connected to the electronic physiological instrument; and (d) detecting a second responsive signal on the at least one data lead and entering the communication mode of operation if the second responsive signal indicates the presence of an auxiliary component.

15. The method of claim 14, wherein the first responsive signal is proportional to an impedance across two of the plurality of therapy leads.

16. The method of claim 15, wherein the normal mode of operation is entered if the impedance falls within a range indicating a patient is connected to the electronic physiological instrument.

17. The method of claim 16, wherein the range is approximately 30 to 300 ohms.

18. The method of claim 14, wherein the second responsive signal contains identification information about the auxiliary component.

19. The method of claim 18, further comprising the step of analyzing the second responsive signal to determine the type of auxiliary component connected to the electronic physiological instrument.

20. The method of claim 19, further comprising entering a test mode of operation if the detected auxiliary component is a test instrument.

* * * * *

UNITED STATES PATENT AND TRADEMARK OFFICE
CERTIFICATE OF CORRECTION

PATENT NO. : 5,716,380
DATED : February 10, 1998
INVENTOR(S) : D. Yerkovich et al.

It is certified that error appears in the above-identified patent and that said Letters Patent is hereby corrected as shown below:

Title page,
Item [56], columns 1-2 References Cited (U.S. Patents), please insert the following references in the appropriate numerical order:

| | | |
|---|---|---|
| -- 4,419,998 | 12/1983 | Heath |
| 4,870,341 | 9/1989 | Pihl et al. |
| 5,148,805 | 9/1992 | Scharnberg |
| 5,405,362 | 4/1995 | Kramer et al. |
| 5,549,646 | 8/1996 | Katz et al. |
| 5,562,713 | 10/1996 | Silvian -- |

Signed and Sealed this

Sixth Day of November, 2001

Attest:

*Nicholas P. Godici*

NICHOLAS P. GODICI
*Attesting Officer*  *Acting Director of the United States Patent and Trademark Office*